United States Patent
Lu et al.

(10) Patent No.: US 10,912,721 B2
(45) Date of Patent: Feb. 9, 2021

(54) THIN EMULSION BASE FOR COSMETICS

(71) Applicant: Juice Beauty, Inc., San Rafael, CA (US)

(72) Inventors: Mimi Lu, San Rafael, CA (US); Karen Behnke, San Rafael, CA (US)

(73) Assignee: JUICE BEAUTY, INC., San Rafael, CA (US)

( * ) Notice: Subject to any disclaimer, the term of this patent is extended or adjusted under 35 U.S.C. 154(b) by 0 days.

(21) Appl. No.: 16/214,627

(22) Filed: Dec. 10, 2018

(65) Prior Publication Data
US 2019/0192390 A1    Jun. 27, 2019

Related U.S. Application Data

(60) Provisional application No. 62/610,056, filed on Dec. 22, 2017.

(51) Int. Cl.

| | | |
|---|---|---|
| *A61K 8/06* | (2006.01) | |
| *A61K 8/37* | (2006.01) | |
| *A61Q 19/00* | (2006.01) | |
| *A61K 8/31* | (2006.01) | |
| *A61K 8/34* | (2006.01) | |
| *A61K 8/365* | (2006.01) | |
| *A61K 8/368* | (2006.01) | |
| *A61K 8/39* | (2006.01) | |
| *A61K 8/55* | (2006.01) | |
| *A61K 8/60* | (2006.01) | |
| *A61K 8/67* | (2006.01) | |
| *A61K 8/9789* | (2017.01) | |
| *A61K 8/64* | (2006.01) | |
| *A61K 8/891* | (2006.01) | |
| *A61K 8/92* | (2006.01) | |
| *A61Q 19/08* | (2006.01) | |

(52) U.S. Cl.
CPC ............... *A61K 8/06* (2013.01); *A61K 8/062* (2013.01); *A61K 8/31* (2013.01); *A61K 8/345* (2013.01); *A61K 8/365* (2013.01); *A61K 8/368* (2013.01); *A61K 8/375* (2013.01); *A61K 8/39* (2013.01); *A61K 8/553* (2013.01); *A61K 8/60* (2013.01); *A61K 8/64* (2013.01); *A61K 8/678* (2013.01); *A61K 8/891* (2013.01); *A61K 8/922* (2013.01); *A61K 8/9789* (2017.08); *A61Q 19/00* (2013.01); *A61Q 19/08* (2013.01)

(58) Field of Classification Search
CPC . A61K 8/06; A61K 8/062; A61K 8/31; A61K 8/553; A61K 8/97; A61K 8/9783; A61K 8/9789; A61K 8/9794; A61Q 19/00
See application file for complete search history.

(56) References Cited

U.S. PATENT DOCUMENTS

| | | |
|---|---|---|
| 4,481,185 A | 11/1984 | Grollier et al. |
| 5,994,414 A | 11/1999 | Franco et al. |
| 2007/0098670 A1* | 5/2007 | Jochim ............ A61Q 1/04 424/74 |

FOREIGN PATENT DOCUMENTS

WO      2007053815 A2     5/2007

OTHER PUBLICATIONS

Distinctive® Emul-Lipid BA technical bulletin (Resources of Nature, Inc., Dec. 31, 2013). (Year: 2013).*
EP18212736.5, "Extended European Search report", dated Apr. 25, 2019, 7 pages.

* cited by examiner

*Primary Examiner* — Michael B. Pallay
(74) *Attorney, Agent, or Firm* — Kilpatrick Townsend & Stockton LLP

(57) ABSTRACT

This invention provides for a thin emulsion base for cosmetic products with low to medium viscosity. The bases are excipients that provide stability to cosmetic products. The thin emulsion bases of this invention are from non-synthetic and non-petroleum based products and comprise over 80% juice derived solvents with the balance being a combination of alkane texture enhancers and lipid emulsifiers.

13 Claims, No Drawings

THIN EMULSION BASE FOR COSMETICS

CROSS-REFERENCES TO RELATED APPLICATIONS

The present application claims priority to U.S. Provisional Patent Application No. 62/610,056, filed on Dec. 22, 2017, which application is incorporated herein by reference in its entirety.

BACKGROUND OF THE INVENTION

There are hundreds of skin care products on the market today designed to provide a variety of benefits and care for hands, feet, body, eyes, face, etc. Emulsions represent an important sector of so-called cosmetic products because they in fact constitute the vehicles for numerous formulations such as creams, milks, make-up, foundations and the like. These emulsions are obtained by using suitable emulsifiers by means of which either emulsions of the oil-in-water type or emulsions of the water-in-oil type can be produced. Because emulsions represent a mixture of two or more materials that are not miscible in each other, they are inherently unstable and eventually, given enough time or energy, will separate into separate phases.

Consequently, many emulsion systems are comprised of synthetic or semi-synthetic materials. However, skin care products which contain such synthetic materials is emulsions vary in effectiveness, and, in addition to being ineffective, many of them can have adverse side effects and can even damage the skin. Unfortunately, few natural emulsifiers are capable of giving emulsions which at one and the same time exhibit good storage stability, good unctuousness, and good spreading power. For example, lecithin produces emulsions of inferior quality and inferior stability compared to the emulsions obtained with the aid of synthetic emulsifiers. There is a need for stable emulsion bases made of naturally occurring and non-synthetic components for cosmetic products.

The present invention solves these problems and more by providing a thin emulsion base, comprising a plant juice aqueous phase, an alkane texture enhancing oil phase, and a lipid emulsifier. Stability tests have in fact shown that even under relatively severe conditions, the emulsions according to the invention exhibit a good appearance, that is to say are of the preferred milky-white semi-transparent appearance, and are of an unctuous texture and sensation, rather than a sticky or tacky feeling on the skin. In addition to possessing cosmetic properties, these thin emulsion bases have proved to be stable as stand-alone formulations.

BRIEF SUMMARY OF THE INVENTION

In one aspect, the present invention provides a thin emulsion base for cosmetic products comprising a solvent, an alkane texture enhancer, and a lipid emulsifier. The solvent is a plant juice derived supernatant having 6-20% carbohydrate content, an acidic pH of between 2.2 to 6.0, and a bacterial cell count of less than 150 CFU/g, wherein the amount of the solvent ranges from 80 to 90% of the total weight of the thin emulsion base. The alkane texture enhancer is a mixture consisting of at least 90% C12 alkanes, less than 10% C14 alkanes, and less than 10% coco-caprylate/caprate, wherein the amount of the alkane texture enhancer ranges from 4.5 to 10.5% of the total weight of the thin emulsion base. The lipid emulsifier is a mixture consisting of 30 to 60% (optionally 50%-60%) polyglyceryl-10 mono/dioleate, 30 to 60% (optionally 30%-40%) polyglyceryl-3 oleate, 3 to 7% glycerin, and 0.5 to 1.5% phosphatidylglycerol, wherein the amount of the lipid emulsifier ranges from 4.5 to 10.5% of the total weight of the thin emulsion base. The weight to weight ratio of the alkane texture enhancer to the lipid emulsifier of the thin emulsion base ranges from 0.8 to 1.2. The thin emulsion base is stable for at least 90 days at 40° C.

In some embodiments, the invention provides a thin emulsion base, wherein the solvent is a plant juice selected from the group consisting of aloe, grape, lemon, and apple. In some embodiments, the solvent of the thin emulsion base has a pH of between 3.0 and 5.0. In some embodiments, the invention provides a thin emulsion base, wherein the alkane texture enhancer consists of coconut alkanes that is 85-90% C12 alkane.

In some embodiments, the thin emulsion base of the invention has a viscosity of between 4,000 to 12,000 cP. In some embodiments, the thin emulsion base of the invention has a specific gravity of between 0.99 to 1.05, wherein the density ratio is in comparison to water at 4° C. and 1 atm. In some embodiments, the thin emulsion base of the invention is stable for at least three cycles of freeze and thawing.

In a related aspect, the invention provides a composition comprising the thin emulsion base as described herein and a floral fragrance. In another aspect, the invention provides a composition comprising the thin emulsion base as described herein and at least one compound selected from the group consisting of caprylic/capric triglyceride, cyclomethicone or dimethicone, glycols, glycerin, and sodium hyaluronate. In another related aspect, the invention provides a composition comprising the thin emulsion base as described herein and at least one compound selected from the group consisting of peptides, xanthan gum, PEGs, ceramides, retinoids (Vit A). In yet another related aspect, the invention provides a composition comprising the thin emulsion base as described herein and at least one compound selected from the group consisting of coco-glucoside, glycerin, PEGs, and decyl glucoside. In a further related aspect, the invention provides a composition comprising the thin emulsion base as described herein and sunflower seed oil and/or tocopherol.

In another aspect, the present invention provides a method of manufacturing a thin emulsion base for cosmetic products by combining a solvent, an alkane texture enhancer, and a lipid emulsifier. The solvent is a plant juice derived supernatant having 6-20% carbohydrate content, an acidic pH of between 2.2 to 6.0, and a bacterial cell count of less than 150 CFU/g, wherein the amount of the solvent ranges from 80 to 90% of the total weight of the thin emulsion base. The alkane texture enhancer is a mixture consisting of at least 90% C12 alkanes, less than 10% C14 alkanes, and less than 10% coco-caprylate/caprate, wherein the amount of the alkane texture enhancer ranges from 4.5 to 10.5% of the total weight of the thin emulsion base. The lipid emulsifier is a mixture consisting of 30 to 60% polyglyceryl-10 mono/dioleate, 30 to 60% polyglyceryl-3 oleate, 3 to 7% glycerin, and 0.5 to 1.5% phosphatidylglycerol, wherein the amount of the lipid emulsifier ranges from 4.5 to 10.5% of the total weight of the thin emulsion base. The weight to weight ratio of the alkane texture enhancer to the lipid emulsifier of the thin emulsion base ranges from 0.8 to 1.2. The resulting thin emulsion base is stable for at least 90 days at 40° C.

DETAILED DESCRIPTION OF THE INVENTION

I. Introduction

This invention provides for a thin emulsion base for cosmetic products having low to medium viscosity. Such bases are excipients that provide stability to cosmetic products. The thin emulsion bases of this invention are from non-synthetic and non-petroleum based products and comprise over 80% juice derived solvent and up to 20% of an alkane texture enhancer and lipid emulsifier mixture. A key feature of this invention is the ratio of alkane texture enhancers to lipid emulsifiers to provide the necessary stability and required after feel and appearance properties.

Using organic juices as a base composition for a skin care product is a costly process with many challenging logistics. For example, seasonal produce, weather sensitivity and the fact that each crop has unique chemistry and colors combine to make the development of juice-based organic skin care products extremely difficult. Implementing a juice-based solvent into an emulsion composition is exceedingly more difficult given the inherent instability of emulsion systems. However, the juice-containing thin emulsion bases described herein prove to be stable over extended periods of time and after exposure to extreme conditions.

Organic juices are rich in potent antioxidants, essential vitamins, vital phyto-nutrients, and powerful hydroxy acids, making them excellent ingredients for skin care products. The emulsion base compositions below do not make use of artificial fillers, toxic preservatives, water to dilute the compositions, tars, petroleum, synthetic fragrances, or parabens.

II. Definitions

The phrase "alkane texture enhancer" refers to a homogeneous three-component mixture of hydrophobic compounds and can be used to produce thin emulsion bases with the solvent and the lipid emulsifier. The alkane texture enhancer contains non-polar oils and polar oils. "Non-polar" oils are generally oils which are hydrocarbons ("alkanes") and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the "solvent" which is used in the thin emulsion base of the present invention. The alkane texture enhancer provides an observable or otherwise detectable improvement in the tactile sensation experienced by touching and/or feeling the thin emulsion base, compared to a thin emulsion base that does not contain the alkane texture enhancer component. Alkane texture enhancer compounds/compositions are described in detail in the present application.

The terms "alkane" and "alkanes" refer to non-aromatic, saturated hydrocarbons with the general formula $C_nH_{(2n+2)}$, wherein n is an integer from, for example, 10 to 22, preferably 12 to 18. The alkanes can exist as a mixture of linear and branched saturated hydrocarbons. Alkanes particularly useful for the alkane texture enhancer of the instant invention, for example, are liquid at room temperature (i.e., 20° C. to 25.5° C.) and are alkanes having 12 and 14 carbons (i.e., C12 and C14, respectively).

The term "floral fragrance" refers to any odoriferous mixture which provides the thin emulsion base and/or cosmetic product compositions comprising the thin emulsion base described herein with a pleasing floral odor. The floral fragrance can include one or two components. Examples of floral fragrances include, but are not limited to, rose, hyacinth, lilac, lily-of-the-valley, calyx, osmanthus, orange blossom, apple blossom, rose, and freesia.

The term "lipid emulsifier" refers to a homogeneous four-component mixture of compounds which contain both hydrophilic and hydrophobic residues and can be used to produce thin emulsion bases with the solvent and the alkane texture enhancer. The lipid emulsifier provides an increased interaction between the water phase ("solvent") and oil phase ("alkane texture enhancer") components of the thin emulsion bases of the invention. Lipid emulsifier compounds/compositions are described in detail in the present application.

The term "plant juice" refers to the water-based liquid that is obtained from any suitable plant or part thereof. Plant juice is the solvent component of the thin emulsion base of the invention.

The term "percent weight," unless otherwise defined, means % or refers to the percentage of a component measured in weight per total weight of a composition. Percent weight is represented by "%" or "% w/w."

The terms "peptide(s)," "polypeptide(s)," and "protein(s)" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. Such amino acid polymers can be incorporated into the cosmetic products described herein which comprise the thin emulsion base of the instant invention.

The term "solvent" refers to the aqueous mixture derived from plant juice and can be used to produce thin emulsion bases with the alkane texture enhancer and the lipid emulsifier.

Solvent compositions are described in detail in the present application.

The phrase "thin emulsion base" refers to the base excipient formulated alongside the active ingredients of a cosmetic product. The thin emulsion base is typically inert and present for the purpose of long-term stabilization of the whole cosmetic product. The solvent, the alkane texture enhancer, and the lipid emulsifier are the three components of the thin emulsion base. The term "thin" is used to define the viscosity of the emulsion base as between 4000 and 12,000 cP. Thin emulsion base compositions are described in detail in the present application.

III. Thin Emulsion Base Compositions

Solvents

The present invention provides a thin emulsion base composition for cosmetic products having a solvent, an alkane texture enhancer, and a lipid emulsifier. The solvent of the thin emulsion base composition is a plant juice. Any suitable plant juice is useful as a solvent in the thin emulsion base, such as, for example, aloe barbadensis leaf juice (aloe), *Vitis vinifera* juice (grape), pyrus malus juice (apple), citrus limon juice (lemon), and citrus aurantium juice (orange). Preferably the solvent is derived from certified organic fruit or plants. Various parts of the plants (i.e., plant biomass) may be used as the solvent. For example, the stems and leaf tissue may be used for many types of plants. For other plants, the flowers or fruit may be used as sources of plant juice for use in the present invention. For example, the fruit tissue of grape, apple, or lemon can be used to obtain the solvent as the plant juice derived supernatant. In another embodiment, the leaf and stem tissue of the aloe plant can be used to obtain the solvent as the plant juice derived supernatant.

The solvent, a plant juice derived supernatant, can be obtained using suitable extracting methods known in the art. However, the extraction technique should result in a plant juice that preserves the bioactive components of the plant. An exemplary method of obtaining the plant juice derived supernatant involves harvesting the suitable plant biomass (i.e., fruit, flower, leaf, stem, etc.), preparing the harvested biomass for the extraction process, and extraction. The extracted plant juice can also be concentrated and reconstituted to obtain a suitable solvent for use in the thin emulsion base.

The plant biomass should be harvested in conditions which avoid moisture loss of the plant biomass. Optimal conditions are those where natural moisture content is maintained and preserved. Harvesting of the plant biomass may be conducted in a manner that avoids or minimizes the chopping, mashing, crushing, or other type of injury of the plant. Delivery time of plant material to the processing facility and exposure of biomass to sun, high temperature, and other negative environmental factors, should be minimized to prevent the impact of unwanted degradation processes. The harvested plant mass should be washed remove the soil particles and other debris from plants prior to grinding and maceration once the plant tissue is harvested.

After the plant biomass is harvested, as described above, the plant biomass is subjected to grinding, maceration, and pressing to extract the intracellular content (i.e., the plant juice derived supernatant, and to separate it from the fiber-enriched press-cake containing predominantly cell walls). For example, a hammer mill may be used to grind the plant biomass to yield plant tissue particles of a small size in a short time and without significant increase of biomass temperature. In one embodiment, a modified hammer mill is used to produce the maximum size of macerated plant particles less than or equal to 0.5 centimeters during less than or equal to 10 seconds of treatment, where the increase of biomass temperature is less than or equal to 5° C. The extraction of the plant juice and its separation from the press-cake is commenced as soon as possible after grinding and maceration of the plant biomass. The plant biomass is processed in a short time and without significant increase in temperature. In one embodiment, immediately after grinding and maceration, the plant biomass is pressed using a horizontal, continuous screw press (Compact Press "CP-6", Vincent Corporation, FL). The pressure on the cone is maintained at level 24 kg/cm$^2$, screw speed is at 12 rpm, and the temperature increase is less than or equal to 5° C.

The initial plant juice supernatant usually contains small fiber particles, which can absorb valuable plant juice components and also block the hoses and pumps. The above particles should be removed by filtration or low-speed centrifugation. For example, the initial plant juices produced after the pressing step are filtered through four layers of nylon fabric. The filtrate is collected and used as the solvent.

The plant juice derived supernatant (i.e., solvent) will have a carbohydrate content that is between about 6% and 20% of the solvent. In some embodiments, the plant juice will have a carbohydrate content that is between about 8% and about 18%, about 10% and about 16%, or about 12% and about 16% of the solvent. In some embodiments, the plant juice will have a carbohydrate content that is about 7%, about 11%, or about 17%.

The plant juice solvent will have an acidic pH that is between about 2.2 and about 6.0. In some embodiments, the plant juice will have an acidic pH that is between about 2.5 and about 5.5, about 3 and about 5, or about 3.5 and about 4.5. In some embodiments, the plant juice will have an acidic pH that is between about 4 and about 5. In other embodiments, the plant juice will have an acidic pH that is about 2.5 or 3.6.

The solvent used in the thin emulsion base of the present invention will also have a bacterial cell count of less than 150 CFU/g (colony forming units per gram of solvent). In some embodiments, the bacterial cell count of the plant juice derived supernatant is between about 0 CFU/g and about 145 CFU/g, between about 30 CFU/g and about 120 CFU/g, or between about 50 CFU/g and about 100 CFU/g. In some embodiments, the plant juice solvent will have a bacterial cell count that is less than 150 CFU/g, less than 100 CFU/g, or less than 50 CFU/g. In some embodiments, the solvent has a bacterial cell count that is less than 100 CFU/g.

A culture-based method can be used to determine the bacterial cell count of the solvent, in which serial dilutions of the plant juice cultures are plated onto agar plates containing the appropriate nutrients and incubated for about 48 hours aerobically at mesophilic temperatures (25 to 40° C., or 35° C., for example). Colonies on the plates are counted and the number of CFUs (colony forming units) in the samples are calculated as CFU/mL or CFU/gram. Methods of determining the CFUs are described in detail below.

In some embodiments, the solvent is a an aloe plant juice derived supernatant having a carbohydrate content of about 11.3%, an acidic pH of between 3 and 5, and a bacterial cell count of less than 100 CFU/g. In some embodiments, the solvent is a grape juice derived supernatant having a carbohydrate content of about 17.4%, an acidic pH of between 4 and 5, and a bacterial cell count of less than 100 CFU/g. In some embodiments, the solvent is an apple juice derived supernatant having a carbohydrate content of about 11.2%, an acidic pH of about 3.6, and a bacterial cell count of less than 100 CFU/g. In some embodiments, the solvent is a lemon juice derived supernatant having a carbohydrate content of about 7%, an acidic pH of about 2.5, and a bacterial cell count of less than 100 CFU/g.

Alkane Texture Enhancers

The alkane texture enhancer component of the thin emulsion base of the invention is used to improve the texture and feel of a cosmetic product containing the thin emulsion base. Cosmetic products which contain the thin emulsion base of the invention will glide upon the skin surface, making the composition smooth and silky to apply. The alkane texture enhancer is a mixture of coconut alkanes (a non-polar oil) and coco-caprylate/caprate (a polar oil). The alkane texture enhancer is a mixture consisting of C12 alkanes, C14 alkanes, and coco-caprylate/caprate.

Coco-caprylate/caprate is an ester derived from a mixture of coconut fatty alcohol oil, caprylic acid, and capric acid. It is a medium spreading emollient that is clear, mildly yellowish, medium polar oil, and a spreading value of approximately 800 mm$^2$/10 min. The coco-caprylate/caprate has a cloud point of 8-15° C., a viscosity of 9-12 cP, and a refraction (20° C.) of 1.4430-1.4470. The ester is prepared from the dehydration of C12-C18 coconut fatty alcohols with C8 caprylic acid and C10 capric acid. The esterification reaction will involve a catalyst, such as sulfuric acid, to form coco-caprylate/caprate from the coconut fatty alcohol and caprylic and capric acids. Because esterification is a reversible reaction, water must be removed to obtain a high-ester yield. One of skill in the art will appreciate the detailed steps and methods of ester synthesis, such as those included in *Bailey's Industrial Oil and Fat Products*, Sixth Edition, Six Volume Set, 2005, John Wiley & Sons, Inc., pages 1-56. Coco-caprylate/caprate is also commercially available and can be purchased from, for example, ABITEC Corporation (Columbus, Ohio), BASF Corporation (Florham Park, N.J.), SEPPIC (Fairfield, N.J.), and Stearinerie Dubois (Boulogne-Billancourt, France).

The alkane texture enhancer is a mixture consisting of at least 90% C12 alkanes, less than 10% C14 alkanes, and less than 10% coco-caprylate/caprate. In some embodiments, the alkane texture enhancer is a mixture consisting of at least 90% C12 alkanes, no more than 4% C14 alkanes, and 6% coco-caprylate/caprate.

Lipid Emulsifiers

The lipid emulsifier component of the thin emulsion base of the invention is used to stabilize the interface between the solvent and alkane texture enhancer. The lipid emulsifier contains both water soluble fatty acids and fat soluble fatty acids, enabling the homogenous dispersal of lipophilic components (i.e., the alkane texture enhancer) and hydrophilic components (i.e., the solvent) throughout the thin emulsion base. In some embodiments, the lipid emulsifier is a mixture of polyglyceryl esters (i.e., polyglyceryl-10 mono/dioleate and polyglyceryl-3 oleate), glycerin, and phosphatidylglycerol.

The lipid emulsifier will contain polyglyceryl esters with between 3 and 10 glyceryl units. Polyglyceryl esters promote the texture homogeneity of the lipid emulsifier and, thus, of the thin emulsion base. The lipid emulsifier contains both polyglyceryl-10 mono/dioleate and polyglyceryl-3 oleate.

Polyglyceryl-10 mono/dioleate is a blended polyglycerol ester, involving a mixture of mono- and diesters of lipophilic oleic acid and a polyglycerin polymer containing an average of ten glycerin units. It has an hydrophilic-lipophilic balance (HLB) of about 11 and acid value ≤6, hydroxyl value ≤400 and saponification value ≤145. The polyglyceryl-10 mono/dioleate mixture for use in the lipid emulsifier is commercially available and can be purchased from, for example, Vantage Specialty Chemicals (Chicago, Ill.) or ABITEC Corporation (Columbus, Ohio). Polyglyceryl-3 oleate is a fatty acid ester of lipophilic oleic acid and polyglycerin-3 with a molecular formula of $C_{36}H_{82}O_{20}$. The polyglyceryl-3 oleate for use in the lipid emulsifier is commercially available and can be purchased from, for example, Vantage Specialty Chemicals (Chicago, Ill.), Evonik Industries (Parsippany, N.J.), or ABITEC Corporation (Columbus, Ohio).

Glycerin, which is also known in the art as glycerol, is a polyhydric alcohol humectant. In some embodiments, glycerin is plant-derived. Glycerin is commercially available and can be purchased from, for example Evonik Industries (Parsippany, N.J.), Spectrum Chemical Mfg. Corp. (New Brunswick, N.J.), or AG Commodities, Inc. (Tustin, Calif.).

Phosphatidylglycerol is a ubiquitous lipid that can be the main component of some bacterial membranes, and it is found also in membranes of plants and animals where it appears to perform specific functions. The charge on the phosphate group means that it is an anionic lipid at neutral pH.

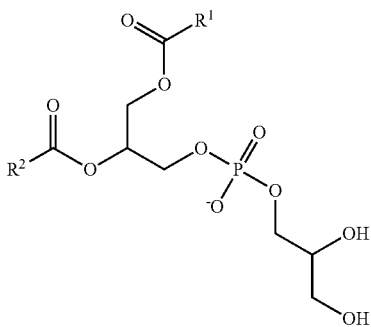

Formula I

Formula I above is the general chemical structure of phosphatidylglycerol, where $R^1$ and $R^2$ are fatty acid side chains. In some embodiments, the $R^1$ and $R^2$ fatty acid chains are independently fatty acid molecules with 4-28 carbons, preferably 13-21 carbons, with 1-8 double bonds, preferably 1 double bond, 2 double bonds, 3 double bonds or 4 double bonds, in cis and/or trans configuration, or any combinations thereof.

In some embodiments, the $R^1$ and $R^2$ fatty acid chains are independently selected from any common fatty acid molecules such as myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

In some embodiments, the phosphatidylglycerol species contains one or more monounsaturated fatty acids. In other embodiments, the phosphatidylglycerol species contains one or more polyunsaturated fatty acids. In some embodiments, the phosphatidylglycerol is egg-derived phosphatidylglycerol, or soy phosphatidylglycerol. Egg-derived phosphatidylglycerol exhibits the following fatty acid composition (with the first number representing the total number of carbon atoms in the fatty acid and the second number, the number of double bonds): 16:0 (34%) 16:1 (2%), 18:0 (11%), 18:1 (32%), 18:2 (18%) and 20:4 (3%). Soy phosphatidylglycerol is a phosphatidylglycerol mixture with a large percentage of polyunsaturated fatty acids, composed of 16:0 (17%), 18:0 (6%), 18:1 (13%), 18:2 (59%), and 18:3 (5%). In some embodiments, phosphatidylglycerol is a phosphatidylglycerol mixture with a large percentage of polyunsaturated fatty acids, composed of 16:0 (12.4%), 18:0 (3.6%), 18:1 (10.5%), 18:2 (65.6%), 18:3 (6.3%).

In one embodiment, the phosphatidylglycerol is dioleoyl-phosphatidylglycerol (two 18-carbon fatty acids with one double bond each, denoted as 18:1/18:1). Exemplary phosphatidylglycerols also include palmitoyl-arachidonyl-phosphatidylglycerol (16:0/20:4), palmitoyl-linoleoyl-phosphatidylglycerol (16:0/18:2), dilinoleoyl-phosphatidylglycerol (18:2/18:2), palmitoyl-oleoyl-phosphatidylglycerol (16:0/18:1), dioleoyl-phosphatidylglycerol (18:1/18:1), and dihexanoylphosphatidylglycerol (DHPG), dipalmitoylphosphatidylglycerol (DPPG), di stearoylphosphatidylglycerol (DSPG), palmitoyl-oleoylphosphatidylglycerol (POPG).

In some embodiments, the phosphatidylglycerol of the lipid emulsifier has the molecular formula $C_{40}H_{71}O_{10}P$. Phosphatidylglycerols for use in the lipid emulsifier are commercially available and can be purchased from, for example, Vantage Specialty Chemicals (Chicago, Ill.) or Avanti Polar Lipids, Inc. (Alabaster, Ala.).

In some embodiments, the lipid emulsifier is a mixture consisting of 30 to 60% (preferably 45% to 55%) polyglyceryl-10 mono/dioleate, 30 to 60% (preferably 45% to 55%) polyglyceryl-3 oleate, 3 to 7% glycerin, and 0.5 to 1.5% phosphatidylglycerol. In some embodiments, the lipid emulsifier is a mixture consisting of 50% polyglyceryl-10 mono/dioleate, 50% polyglyceryl-3 oleate, 5% glycerin, and 1.0% phosphatidylglycerol.

IV. Thin Emulsion Base Formulations

In some embodiments, the thin emulsion base for cosmetic products includes suitable amounts of a solvent, an alkane texture enhancer, and a lipid emulsifier, as described herein. In some embodiments, the thin emulsion base contains about 80 to 90% of the solvent. In some embodiments, the thin emulsion base contains about 81 to 89% of the solvent, about 82 to 88%, about 83 to 87%, or about 84 to 86% of the solvent. In some embodiments, the thin emulsion base contains about 85 to 86% of the solvent.

In some embodiments, the thin emulsion base contains about 4.5 to 10.5% of the alkane texture enhancer. In some embodiments, the thin emulsion base contains about 4.5 to 10% of the alkane texture enhancer, about 5 to 10%, about 5 to 9.5%, about 5.5 to 9%, about 5.5 to 8.5%, or about 6 to 8% of the alkane texture enhancer. In some embodiments, the thin emulsion base contains about 7 to 8% of the alkane texture enhancer.

In some embodiments, the thin emulsion base contains about 4.5 to 10.5% of the lipid emulsifier. In some embodiments, the thin emulsion base contains about 4.5 to 10% of the lipid emulsifier, about 5 to 10%, about 5 to 9.5%, about 5.5 to 9%, about 5.5 to 8.5%, or about 6 to 8% of the lipid emulsifier. In some embodiments, the thin emulsion base contains about 7 to 8% of the lipid emulsifier.

The weight to weight ratio of the alkane texture enhancer to the lipid emulsifier of the thin emulsion base of the invention will range from 0.8 to 1.2. For example, a thin emulsion base containing 90% of the plant juice solvent, can also have 4.5% of alkane texture enhancer and 5.5% of lipid emulsifier. Thus, the weight to weight ratio of the alkane texture enhancer to the lipid emulsifier is 0.81 (i.e., 4.5:5.5=0.81). As a further example, a thin emulsion base with 80% solvent can also contain 10.5% of alkane texture enhancer and 9.5% of lipid emulsifier. In this case, the weight to weight ratio of the alkane texture enhancer to the lipid emulsifier is 1.11 (i.e., 10.5:9.5=1.11). In some embodiments, the weight to weight ratio of the alkane texture enhancer to the lipid emulsifier of the thin emulsion base is 1. The combined weight percent of the alkane texture enhancer and the lipid emulsifier in the thin emulsion base compositions of the invention must be at least 10% of the total weight of the thin emulsion base. Moreover, the combined weight percent of the alkane texture enhancer and the lipid emulsifier in the thin emulsion base compositions of the invention must not exceed 20% of the total weight of the thin emulsion base.

In some embodiments, the thin emulsion base for cosmetic products comprises the solvent in the amount of about 80 to 90%, the alkane texture enhancer in the amount of about 4.5 to 10.5%, and the lipid emulsifier in the amount of about 4.5 to 10.5%. In some embodiments, the thin emulsion base for cosmetic products comprises the solvent in the amount of about 85 to 86%, the alkane texture enhancer in the amount of about 7 to 8%, and the lipid emulsifier in the amount of about 7 to 8%.

The stand-alone thin emulsion bases of the invention can be prepared using customary methods and equipment known by those of skill in the art for preparing skin care products and cosmetics. For example, the plant juice solvent may be physically combined with the alkane texture enhancer and the lipid emulsifier to achieve the weight percent compositions described herein by combining together the individual components. The combined ingredients are emulsified by stirring together the mixture of solvent, alkane texture enhancer, and lipid emulsifier, using sufficient agitation to achieve relative homogeneity of the oil-in-water emulsion. Agitation may be achieved, for example, using a standard mixer, at a slow, moderate or even vigorous speed.

In some embodiments, the mixture comprising the solvent, alkane texture enhancer, and lipid emulsifier can be emulsified using conventional equipment such as a homogenizer, colloidal mill, line mixer, sonolator, combination mixer, Turello mixer, or homogenizer-mixer. In this procedure, after coarse emulsification in an emulsifier, such as a homogenizer, colloidal mill, or line mixer, subsequent fine emulsification may be performed in a pressurized homogenizer or an ultrasonic homogenizer.

The mixture comprising the solvent, alkane texture enhancer, and lipid emulsifier is typically emulsified at a temperature of from 5 to 75° C., alternatively from 5 to 40° C.

The emulsification time depends on many factors, including the type of plant juice, the compositions of the alkane texture enhancer and the lipid emulsifier, the additional active ingredients (described below), temperature, and type of equipment used to emulsify the mixture. The mixture is typically emulsified for a period of time sufficient to produce particles of the alkane texture enhancer having a size of from 100 to 5,000 nm, alternatively from 200 to 3,000 nm, alternatively from 300 to 1,000 nm. For example, the mixture is typically emulsified for a period of from 5 to 60 min., alternatively from 5 to 45 min., or alternatively from 5 to 30 min. In some embodiments, the mixture is emulsified until the thin emulsion base has the desired stability, texture, feel and finish. In some embodiments, the mixture is emulsified for about 30 minutes before combining the then emulsion base with active ingredients.

In some embodiments, the thin emulsion base can be combined with a fragrance. In some embodiments, the fragrance is a fruit fragrance. In some embodiments, the fragrance is a floral fragrance. The fragrance ingredients combined with emulsions of the present invention are the conventional ones known in the art. Suitable fragrance compounds and compositions can be found in the art including U.S. Pat. No. 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; U.S. Pat. No. 4,152,272, Young, issued May 1, 1979; U.S. Pat. No. 5,378,468 Suffis et al., U.S. Pat. No. 5,081,000 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued. Dec. 18, 1973; JP 07-179,328 published Jul. 18, 1995; JP 05-230496 published Sep. 7, 1993; WO 9638528 published Dec. 5, 1996; "WO 96/14827 published May 23, 1996; WO 95/04809 published Feb. 16, 1995; and WO 95/16660 published Jun. 22, 1995; all of said U.S. patents and U.S. references being incorporated herein by reference. In addition P. M. Muller, D Lamparsky *Perfumes Art, Science, & Technology* Blackie Academic & Professional, (New York, 1994) is included herein by reference.

A suitable fragrance, and more specifically, a suitable fragrance, can be a formulation containing more than one individual ingredient. Typically, commercial fragrances may contain from 20 to 200 individual ingredients. In some embodiments, desirable fragrances can be formulated from groups of 2 to 20 ingredients or 2 to 10 ingredients. In some embodiments, the fragrance composition can have at least two fragrance materials selected from: allyl caproate, benzyl acetate, benzaldehyde, benzyl salicylate, dihydroisojasmonate, ethyl cinnamate, ethyl methyl phenyl glycidate, ethyl vanillin, geranyl acetate, heliotropine, cis-hex-3-en-1-ol, ethylene brassylate, nonalactone gamma, camphylcyclohexanol, undecalactone gamma, 2-t-butylcyclohexylacetate, amyl acetate, amyl benzoate, pentyl salicylate, citronellol, citronellyl acetate, cyclamen aldehyde, pentadecalactone, delta decalactone, decanal, ethyl phenethylacetal, ethyl pelargonate, 2-heptylcyclopentanone, hexanol, hinokitiol, geraniol, isobutyl benzoate, linalool, linalyl acetate, menthyl acetate, methyldihydrojasmonate, phenylethanol, phenylethylacetate, phenyl salicylate, terpineol, triacetin, vanillin, 2-phenylethanol, and 2-phenylethyl acetate. The fragrance composition may also contain natural extracts, such as essential oils (e.g., triethyl citrate, citrus aurantium dulcis, and citrus aurantium bergamia).

In some embodiments, the fragrance composition can contain at least two of the following fragrance materials: allyl caproate, benzyl acetate, benzaldehyde, dihydroisojasmonate, ethyl phenethylacetal, ethyl cinnamate, ethyl methyl phenyl glycidate, ethyl vanillin, 2-heptylcyclopentanone, geranyl acetate, heliotropine, cis-hex-3-en-1-ol, ethylene brassylate, nonalactone gamma, camphylcyclohexanol, undecalactone gamma, 2-t-butylcyclohexylacetate, pentyl salicylate, 2-phenylethanol, hinokitiol and 2-phenylethyl acetate.

In some embodiments, the floral fragrance comprises a combination of two or more of the following materials: ethyl pelargonate, ethyl vanillin, heliotropine, phenoxyethanol, Santalex® T ((1,7,7-Trimethylbicyclo[2.2.1]hept-2-yl)-cyclohexanol), ethylene brassylate, isopropyl myristate, terpineol, dihydroisojasmonate, isoamyl acetate, benzyl acetate, cis-hex-3-en-1-ol, undecalactone gamma, amyl salicylate, fleuramone, efetaal, hinokitiol, ethyl cinnamate, ethyl methyl phenyl glycidate, phenylethyl acetate, phenyl ethyl alcohol.

In some embodiments, the floral fragrance comprises amyl salicylate, ethyl cinnamate, ethyl methyl phenyl glycidate, fleuramone, efetaal. In other embodiments, the floral fragrance comprises hinokitiol, ethyl cinnamate, ethyl methyl phenyl glycidate, phenylethyl acetate, phenyl ethyl alcohol.

In some embodiments, the floral fragrance is a floral rose fragrance, comprising the following ingredients: ethyl pelargonate, ethyl vanillin, heliotropine, phenoxyethanol, Santalex® T, ethylene brassylate, isopropyl myristate, terpineol. In some embodiments, the floral fragrance is a floral jasmine fragrance comprising the following ingredients: benzyl acetate, dihydroisojasmonate, cis-hex-3-en-1-ol, isoamyl acetate, ethylene brassylate, Santalex® T, isopropyl myristate, undecalactone gamma. In other embodiments, the floral jasmine fragrance comprises benzyl acetate, heliotropine, cis-hex-3-en-1-ol, ethylene brassylate, phenoxyethanol, Santalex® T, isopropyl myristate, undecalactone gamma.

In some embodiments, the thin emulsion base can be combined with a floral fragrance which can be a blend of essential oils and aromatic extracts commercially available and known in the art. Fragrances can be purchased from, for example, Carrubba, Inc. (Milford, Conn.), Givaudan S. A. (Vernier, Switzerland), International Flavors & Fragrances, Inc. (New York City, N.Y.), or The Lebermuth Company (South Bend, Ind.).

V. Active Ingredients

The thin emulsion bases of the invention can be used in combination with a variety of active ingredients to form various cosmetic products. The active ingredients that are combined with the thin emulsion base will depend on the intended use of the cosmetic product and its function (e.g., moisturizer, cleanser, acne treatment, anti-wrinkle, etc.). Non-limiting examples of cosmetic products that can include the thin emulsion base of the invention include treatment serums, firming serums and cleansers. Each of these products contain active ingredients as described below.

Treatment Serums

Treatment serums are skincare products applied to the face after cleansing but before moisturizing. They contains a powerful level of active ingredients able to be readily absorbed by the skin due to its smaller particle size. Traditional serums are water-based. In some embodiments, the treatment serum comprises at least one of the following ingredients: caprylic/capric triglycerides, cyclomethicone, dimethicone, glycols (e.g., hexylene glycol, pentylene glycol, butylene glycol, and propylene glycol), glycerin, and sodium hyaluronate.

In some embodiments, a cosmetic product can include the thin emulsion base of the invention combined with a treatment serum, wherein the amount of the thin emulsion base can range from about 5 to about 95% of the total weight of the cosmetic product treatment serum. In some embodiments, the amount of the thin emulsion base of a treatment serum-containing cosmetic product can range from about 10 to about 80% of the total weight of the cosmetic product treatment serum, or from about 20 to about 70%, or from about 30 to about 60%, or from about 40 to about 50% of the total weight of the cosmetic product treatment serum. In some embodiments, the amount of the thin emulsion base of a treatment serum-containing cosmetic product can range from about 50 to about 60% of the total weight of the cosmetic product treatment serum.

Firming Serums

Firming serums are a specific type of treatment serum. They help achieve a healthy, youthful look by smoothing the outer appearance of wrinkles and fine lines while they strengthen skin from the inside out. In some embodiments, the firming serum comprises at least one of the following ingredients: peptides, xanthan gum, PEGs (e.g., polyethylene glycols having an average molecular weight of from 100 to 300 and from 1000 to 9000), ceramides, retinoids (e.g., Vitamin A), hyaluronic acid, sodium hyaluronate, and collagen.

In some embodiments, a cosmetic product can include the thin emulsion base of the invention combined with a firming serum, wherein the amount of the thin emulsion base can range from about 5 to about 95% of the total weight of the cosmetic product firming serum. In some embodiments, the amount of the thin emulsion base of a firming serum-containing cosmetic product can range from about 10 to about 80% of the total weight of the cosmetic product firming serum, or from about 20 to about 70%, or from about 30 to about 60%, or from about 40 to about 50% of the total weight of the cosmetic product firming serum. In some embodiments, the amount of the thin emulsion base of a firming serum-containing cosmetic product can range from about 50 to about 60% of the total weight of the cosmetic product firming serum.

Cleansers

Cleansers are facial care products used to remove make-up, dead skin cells, oil, dirt, and other types of pollutants from the face. They are intended to help to unclog pores and create a clean surface area for application of a treatment serum and moisturizer to follow. Cleansers can be formulated with a thin emulsion base in the form of a light lotion or cream. Cleaners can also be combined with the thin emulsion base of the invention in the form of a gel, a foam, or an oil. In some embodiments, cleansers comprise at least one of the following ingredients: coco-glucoside, glycerin, PEGs (e.g., polyethylene glycols having an average molecular weight of from 100 to 300 and from 1000 to 9000), decyl glucoside, sodium lauroamphoacetate, sodium methyl cocoyl taurate, and sodium cocoyl glycinate.

In some embodiments, a cosmetic product can include the thin emulsion base of the invention combined with a cleanser, wherein the amount of the thin emulsion base can range from about 5 to about 60% of the total weight of the cosmetic product cleanser. In some embodiments, the amount of the thin emulsion base of a cleanser-containing cosmetic product can range from about 10 to about 55% of the total weight of the cosmetic product cleanser, or from about 15 to about 50%, or from about 20 to about 45%, or from about 25 to about 40%, or from about 30 to about 35% of the total weight of the cosmetic product cleanser. In some embodiments, the amount of the thin emulsion base of a cleanser-containing cosmetic product can range from about 10 to about 40% of the total weight of the cosmetic product cleanser.

Other active ingredients typically found in cosmetic products include floral fragrances (as described above), plant oils such as sunflower and safflower oils, plant extracts such as rice and linseed extracts, vitamins such as Vitamin A, C, E, and B5, and antioxidants such as tocopherols including alpha-, beta-, gamma- and delta-tocopherols.

VI. Evaluation of Properties

The thin emulsion base compositions of the invention will be tested for preferred physical and chemical properties. In some embodiments, the thin emulsion base composition is qualitatively assessed for its appearance, texture, and aroma. The viscosity and stability of the thin emulsion base compositions are also evaluated. In some embodiments, the properties of the thin emulsion base can be evaluated before combining with active ingredients, after combining with active ingredients, or both before and after the addition of active ingredients. Commercial services, such as, for example, Avomeen Analytic Services (Ann Arbor, Mich.) and Bioscreen Testing Services, Inc. (Torrance, Calif.), are available for evaluating the appearance, texture, aroma, viscosity, and stability of the thin emulsion base compositions of the invention.

Appearance

The thin emulsion bases of this invention will have the desired visual aesthetics and optical properties. In some embodiments, the thin emulsion base can be translucent or transparent. As used herein, "transparency" or "translucency" refer to an appearance of text through the thin emulsion base. In some embodiments, the thin emulsion base can be opalescent, exhibiting a milky iridescent appearance of a dense transparent medium when illuminated by polychromatic visible radiation (e.g., sunlight). In some embodiments the thin emulsion base can be opaque and clear (i.e., free of color), white, or off-white to minimize the appearance of the final cosmetic product.

The desired milky white appearance of the thin emulsion base is due to the difference of refractive index between the hydrophilic phase and the lipophilic phase, leading to scattering of visible light. In some embodiments, the desired visual aesthetics and optical properties can be assessed using the human eye. One approach to creating a translucent or transparent emulsion is to match the refractive index of the two immiscible phases. Generally, to match the refractive index, the refractive difference between the two immiscible phases is only allowed to be about ±0.001-0.005.

The amount of transparency or translucency of the thin emulsion base can be measured using a chromameter, which measures the absolute numbers in XYZ color spaces. A 0.2 mm film of a sample is drawn down and the luminance, Y, is measured on black and white color tiles. The percent (%) transparency is obtained using the following calculation: $100*(1-(Yblack/Ywhite))$. A percent transparency of greater than about 83% is considered transparent. A percent transparency of less than about 83% is not considered transparent. For example, the transparency is measured using a chromameter such as the Spectramagic NX Chromameter available from Konica Minolta Sensing Americas, Inc. (Ramsey, N.J.). Minor differences in transparency, for example about 0.8% transparency, as measured by the chromameter, can be perceivable by the human eye.

Texture

The thin emulsion bases of this invention will have the desired tactile properties and physical feel. The thin emulsion base of the invention is pliable and has acceptable flow (shear-thinning). The thin emulsion base compositions form a soft, smooth film on the skin's surface. The texture of a cosmetically acceptable thin emulsion base will not have a texture that is waxy, tacky, heavy, or draggy. Rather, the texture of a cosmetically acceptable thin emulsion base will have a creamy, smooth, glossy and lightweight texture, permitting easy application to the skin and feathering. Sensorial analysis of the thin emulsion base can be performed using a descriptive test and reference scale to establish the sensory profile of the thin emulsion base. One of skill in the cosmetic arts will be familiar with such evaluations, such as those found in the *Handbook of Cosmetic Science and Technology*, edited by A. O. Barel, M. Paye and H. I. Maibach; Published by Marcel Dekker, Inc. 200—Sensory Testing, Chapter 71, by Linda Oddo and Kathy Shannon, pages 845-857.

Fragrance Stability

One of skill in the art will appreciate the fact that fragrance, as an ingredient, can react with the other ingredients included in a cosmetic product, many of which can result in undesirable changes to a product's odor, solubility, clarity, color, viscosity, or pH. Environmental conditions, such as, temperature, humidity and light, can accelerate these reactions. To assess the fragrance stability of thin emulsion base compositions, these environmental changes can be simulated in a lab setting to predict the compatibility and stability of fragrances in application.

Stability tests can be routinely conducted in conditions which represent potential storage conditions are used to predict long term stability, including ultra violet light, to reproduce the effects of sun and shop lights, as well as an oven, which offers an accelerated assessment of long term stability.

To test the stability of fragrances contained in a thin emulsion base composition, the fragrance-free thin emulsion base should be tested as well as the fragrance-containing thin emulsion base. The test control will help determine the role the fragrance is having on product stability. When the samples are reviewed for odor, the order in which they are smelled can contribute to the results, for example the sample smelled first usually appears to be the strongest. The preferred order for smelling stability samples relates to the relative stability of the storage conditions. For example, refrigerated samples are tested (i.e., smelled) first, followed by samples stored at ambient samples. Samples stored in the oven will be tested after evaluating the fragrance stability of samples stored at ambient temperatures. Samples stored in UV light will be assessed last. Additionally, all of the fragrance-free samples will be tested prior to evaluating the fragrance-containing samples. After a suitable incubation period, the samples will be tested for aromatic stability. No significant loss or changes in quality of aroma is the desired end point.

Viscosity

The thin emulsion bases of this invention are intended as a principle excipient of a variety of different low viscosity cosmetic products. In general, the viscosity of a fluid is a measure of its resistance to gradual deformation by shear stress or tensile stress. For liquids, it corresponds to the informal concept of "thickness," for example, honey has a much higher viscosity than water. Viscosity is more commonly expressed, particularly in American Society for Testing Materials (ASTM) standards, as centipoise (cP). Centipoise is equal to the SI multiple millipascal seconds (mPa·s). For example, water at 20° C. has a viscosity of 1.002 mPa·s=1.002 cP.

Viscometers are used to measure the viscosity of a fluid under defined flow conditions and at given shear rates. They measure the drag caused by the interaction between the fluid and the object surface. The viscometer rotates a sensing tool in a fluid and measures the torque needed to overcome the viscous resistance to the induced movement, by driving the immersed tool (i.e., the spindle), through a beryllium copper spring. The degree to which the spring is wound is proportional to the viscosity of the fluid. For a material of given viscosity, the resistance will be greater as the spindle size and/or rotational speed increase. Viscosities of the thin emulsion base compositions can be determined using a conventional viscometer. For example, Brookfield Viscometers are the most common viscometers used in the cosmetic products and beauty industry to measure viscosity.

In some embodiments, the viscosity of the thin emulsion base composition is between about 2,000 and 70,000 cP. In some embodiments, the viscosity of the thin emulsion base is between about 4,000 and 60,000 cP, about 6,000 and 40,000 cP, about 8,000 and 20,000 cP, or between about 10,000 and 16,000 cP. In some embodiments, the viscosity of the thin emulsion base composition is between about 4,000 and 12,000 cP.

Temperature Stability

Stability can be measured by a variety of methods according to the cosmetic arts. High temperature testing can be used as a predictor of long-term stability for the thin emulsion base and/or cosmetic products containing the thin emulsion bases. In general, reaction rates double for every 10° C. Assuming room temperature to be 25° C., then two years at room temperature would correspond to three months at 45° C., or one month at 50° C. While unfavorable reactions between ingredients in the tested cosmetic compositions can occur at 50° C., such reactions would not be expected to occur to the product in its normal lifecycle. Confidence in the stability of a thin emulsion base can reasonably be placed in a composition that passes a 50° C. test; however, a product that fails at 50° C. may still be considered stable and suitable for the marketplace. Other commonly employed temperature conditions include low temperatures (4° C.), subfreezing temperatures (−20° C.), and freeze-thaw cycles. These tests attempt to simulate all the shipping and storage conditions that can occur in all seasons through the entire region to be served.

The thin emulsion bases can also be tested for stability by first warming a sample to 50° C., for example, and then centrifuging the sample at 3000 rpm for 30 minutes. Separation of emulsions can occur due to differences in specific gravity between the discrete and continuous phases of each thin emulsion base component and the centrifuge increases this gravitational effect.

The stand-alone thin emulsion bases of the invention have improved stability compared to otherwise identical natural-based cosmetic emulsions not containing the plant juice solvent, the alkane texture enhancer, and the lipid emulsifier as described herein. In some embodiments, a test of stability can be performed by heating the test composition to about 40° C. for a period of time such as overnight, one day, two days, three days, four days, five days, six days, one week, two weeks, three weeks, a month, or the like. Alternatively, a test of stability can be performed by heating the test composition to about 60° C. for one hour, six hours, twelve hours, 18 hours, one day, two days, three days, four days, five days, six days, one week, two weeks, three weeks, a month, or the like. In some embodiments, stability is tested by performing one or more freeze/thaw cycles. Evaluation of stability can be by qualitative visual inspection or may be numerically calibrated by measuring the size of separation between phases or through the growth of separation bands. In some embodiments, a stable thin emulsion base has no visible separation. By "otherwise identical" is meant that the individual components and the amounts of components are the same with the exception of the excluded material, which can be proportionally replaced by all of the remaining components, or replaced in whole by the predominant component, for example, the organic plant juice solvent or the lipid emulsifier.

In some embodiments, the thin emulsion bases are placed into a clear vial and incubated in a controlled temperature at a variety of different temperatures such as 25° C., 40° C. or 45° C. for a set period of times. The time may be from 1 week to 12 weeks. At the end of the incubation period the vials are inspected for separation of the emulsion into an aqueous and oil phase. In addition to separation the vials are inspected for color changes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

VII. EXAMPLES

The following examples are provided by way of illustration only and not by way of limitation. Those of skill will readily recognize a variety of noncritical parameters which could be changed or modified to yield essentially similar results.

Example 1

Synthesis of the Milky-White Thin Emulsion Base

Thin emulsion bases of this invention were prepared by first adding the organic aloe plant juice (55-65% of the total cosmetic, pH 3-5, micro APC <100 cfu/g, ~11.3% carbohydrates), purchased from Aloecorp, Inc. (Tacoma, Wash.), to the main kettle of a mixer. The solvent was heated to 75° C. The alkane texture enhancer (5% of the total cosmetic, Vegelight 1214LC), purchased from Grant Industries, Inc. (Elmwood Park, N.J.), and the lipid emulsifier (5% of the total cosmetic, Distinctive Emul-lipid BA), purchased from Vantage Specialty Chemicals (Chicago, Ill.) were combined together in the side kettle of the mixer and mixed together at a moderate speed while heating to 75° C. Once the alkane texture enhancer-lipid emulsifier mixture reached a temperature of 75° C., the mixture was slowly added to the solvent in the main kettle while mixing at high speed at 75° C. for 30 minutes until completely homogenized. The emulsified mixture was allowed to cool to room temperature while continuing to mix at moderate intensity until the emulsion reached a temperature of about 25° C. (or room temperature). This is the process that is used to form the thin emulsion base of the instant invention.

To form a final cosmetic product that contains the thin emulsion base of the invention, the fragrance and the active ingredients of the cosmetic product were added to the thin emulsion base emulsion during the cool down phase described above. In other words, the fragrance and the active ingredients were combined with the emulsified mixture of the solvent, alkane texture enhancer, and lipid emulsifier while the emulsion was cooling down from 75° C. to about 25° C. Mixing at a moderate intensity was continued until the final cosmetic product mixture was completely homogenized and reached a temperature of about 25° C. (or room temperature) Above percentages are for a final cosmetic product.

The percent weight ratio of the final thin emulsion base net of all other ingredients was 85-86% organic aloe juice solvent, 7-8% alkane texture enhancer, and 7-8% lipid emulsifier. The viscosity was between 4,000-12,000 cPs, as measured using a Brookfield Viscometer LVT (spindle #4, 10 rpm, method TM-002). Specific gravity at 25° C. was between 0.99-1.05, as measured using a Cole Parmer specific gravity cup. The final outcome of the thin emulsion base had the desired stability, texture, feel and finish. The thin emulsion base had a milky, white and off-white color. The texture was smooth and silky to the touch. The thin emulsion base was easily spreadable and glided across the skin surface. The skin appeared brighter and having a reflectance, rather than dry and/or sticky.

Example 2

Formulation and Stability Studies of Milky-White Thin Emulsion Bases

The following example demonstrates the development and identification of a thin emulsion base formulation that is stable for at least 90 days at 40° C. In this example, the ingredients of the final formulation identified in Example 1 remained the same for each of the formulation and stability experiments shown below in Table 1 (experiments 1-15), but the ingredient amounts were varied. This procedure was used to establish critical amounts of the solvent, alkane texture enhancer, lipid emulsifier, and ratios thereof for an optimized thin emulsion base formulation with desired stability.

TABLE 1

Thin emulsion base stability and criticality tests

| Exp. | Solvent, % | ATE[a], % | LE[b], % | ATE:LE | Result |
|---|---|---|---|---|---|
| 1* | 85.7 | 7.15 | 7.15 | 1.0 | stable |
| 2 | 85 | 8 | 7 | 1.14 | unstable |
| 3 | 85 | 9 | 6 | 1.5 | unstable |
| 4 | 85 | 6 | 9 | 0.67 | unstable |
| 5 | 75 | 10.5 | 14.5 | 0.72 | unstable |
| 6 | 75 | 14.5 | 10.5 | 1.38 | unstable |
| 7 | 75 | 12.5 | 12.5 | 1.0 | unstable |
| 8 | 85 | 11 | 4 | 2.75 | unstable |
| 9 | 86 | 3.5 | 10.5 | 0.33 | unstable |
| 10 | 80 | 11 | 9 | 1.22 | unstable |
| 11 | 80 | 9 | 11 | 0.82 | unstable |
| 12 | 83.5 | 5 | 11.5 | 0.43 | unstable |
| 13 | 87 | 9 | 4 | 2.25 | unstable |
| 14 | 93.5 | 3.5 | 3 | 1.17 | unstable |
| 15 | 85 | 7 | 8 | 0.875 | unstable |

*Final thin emulsion base formulation;
[a]ATE = Alkane texture enhancer;
[b]LE = Lipid emulsifier Each thin emulsion base formulation of Table 1 was prepared as described in Example 1 and then challenged in industry standard stability testing packaging at 25° C. and 40° C. The stability testing packaging is a glass jar with screw top lid. A sample of each formulation of Table 1 was stored at each temperature (25° C. and 40° C.) for a 90 day time period, and evaluated during the storage period at 1 week, 2 weeks, 4 weeks, 8 weeks, and 12 weeks. At each evaluation time point, the formula samples were qualitatively assessed for formula appearance, formula odor, and packaging appearance. A formulation was determined to be unstable if at any point during the stability testing period a change in formula appearance, formula odor, and/or packaging appearance was observed at either 25° C. or 40° C. Conversely, a formulation was determined to be stable if no change in formula appearance, formula odor, and/or packaging appearance was observed at both 25° C. and 40° C. at any evaluation time point during the 90 day period.

The initial appearance of each of the 15 thin emulsion base formulations tested was the desired homogenous milky-white lotion color. As shown in Table 1, the only thin emulsion base formulation to pass the stability testing at both 25° C. and 40° C. for the entire 90 day period was the formulation of experiment 1. This is the only formulation that remained a completely homogenous milky-white colored lotion. In other words, no separation was observed in the sample of formulation 1 stored at 25° C. or in the sample of formulation 1 stored in the accelerated oven chamber at 40° C. for the full testing period (12 weeks).

The remaining formulations 2-15 failed the stability test due to visible formulation separation (e.g., film formation of more than 3 mm) that was observed during the stability testing period. For example, the formulation of experiment 2 separated after 2 weeks at both 25° C. and 40° C., while the formulation of experiment 15 also separated at both temperatures after about 4 weeks. The formulations of experiments 3, 4, 6, 9, 10 and 14 not only separated during the 90 day period, but also resulted in mold formation. Therefore, the results of the stability tests for each of the 15 thin emulsion base formulations of the formulation optimization study confirmed that the thin emulsion base formulation comprising 85-86% organic aloe juice solvent, 7-8% alkane texture enhancer, and 7-8% lipid emulsifier, with a weight to weight ratio of the alkane texture enhancer to the lipid emulsifier of the thin emulsion base of 1, is the optimized thin emulsion base formulation.

Example 3

Cosmetic Formulations of Stable Thin Emulsion Bases

The following example demonstrates the stability of a final cosmetic product that contains a stable thin emulsion base. In this example, the fragrance and the active ingredients for a firming serum cosmetic product were combined with the thin emulsion base formulation 1 (Table 1, Example 2), as described in Example 1, to form the firming serum cosmetic products of Table 2 (below). These firming serums were subjected to temperature and microbial challenges, detailed below, to confirm desired stability of the final cosmetic product containing a thin emulsion base formulation of the invention.

TABLE 2

Stable firming serum cosmetics containing a stable thin emulsion base

| Exp. | Solvent, % | ATE$^a$, % | LE$^b$, % | ATE:LE | Fragrance |
|---|---|---|---|---|---|
| 1 | 55-65 | 5.0 | 5.0 | 1.0 | 0.6$^c$ |
| 2* | 55-65 | 5.0 | 5.0 | 1.0 | 0.5$^d$ |

All percentages are weight % to the entire cosmetic product;
*Final firming serum cosmetic product;
$^a$ATE = Alkane texture enhancer;
$^b$LE = Lipid emulsifier;
$^c$triethyl citrate and citrus aurantium dulcis;
$^d$triethyl citrate, citrus aurantium dulcis, and citrus aurantium bergamia The firming serum cosmetic formulations of Table 2 were challenged in final commercial packaging at both 25° C. and 40° C. for a day 90 time period, as described previously in Example 2. The final commercial packaging is a 30 mL glass bottle with an auto-priming dropper. The dropper has a button that self-loads when the cap is twisted to open and close. A sample of each firming serum was also challenged in its final commercial packaging against three freeze-thaw cycles. The freeze-thaw test involved freezing a sample for 24 hours, thawing the sample to room temperature for 24 hours, and repeating two more times before qualitatively assessing the stability. A firming serum cosmetic product was determined to be stable against temperature challenges if no change in cosmetic product appearance, cosmetic product odor, and/or packaging appearance was observed after the temperature challenges. The firming serum cosmetic products 1 and 2 (Table 2) were stable after three freeze-thaw cycles and at both 25° C. and 40° C. at each evaluation time point during the 90 day period.

Furthermore, no evidence was found of product leaching for firming serum 2 and only minimal weight loss was observed (0.01% average weight loss at 25° C. for 12 weeks; 0.02% average weight loss at 40° C. for 12 weeks). Firming serum 2 (Table 2) was also an effective system exerting antimicrobial effectiveness, passing preservative challenge testing. The antimicrobial effectiveness was tested using the known United States Pharmacopeia TM-03 method (USP 38-2015, Antimicrobial Effectiveness Testing <51>).

What is claimed is:

1. A thin emulsion base for cosmetic products comprising a solvent, an alkane texture enhancer, and a lipid emulsifier, wherein:
   i) the solvent is a plant juice derived supernatant having 6-20% w/w carbohydrate content, an acidic pH of between 2.2 to 6.0, and a bacterial cell count of less than 150 CFU/g, wherein the amount of the solvent ranges from 85 to 86% w/w of the total weight of the thin emulsion base;
   ii) the alkane texture enhancer is a mixture consisting of at least 90% w/w C12 alkanes, less than 10% w/w C14 alkanes, and less than 10% w/w coco-caprylate/caprate;
   iii) the lipid emulsifier is a mixture consisting of 30 to 60% w/w polyglyceryl-10 mono/dioleate, 30 to 60% w/w polyglyceryl-3 oleate, 3 to 7% w/w glycerin, and 0.5 to 1.5% w/w phosphatidylglycerol;
   wherein the weight to weight ratio of the alkane texture enhancer to the lipid emulsifier of the thin emulsion base is 1; and
   wherein the thin emulsion base is stable for at least 90 days at 40° C.

2. The thin emulsion base of claim 1, wherein the solvent is a plant juice selected from the group consisting of aloe, grape, lemon, and apple.

3. The thin emulsion base of claim 1, wherein the solvent has a pH of between 3.0 and 5.0.

4. The thin emulsion base of claim 1, wherein the alkane texture enhancer consists of coconut alkanes that is 85-90% w/w C12 alkane.

5. The thin emulsion base of claim 1, wherein the base has a specific gravity of between 0.99 to 1.05 and wherein the density ratio is in comparison to water at 4° C. and 1 atm.

6. The thin emulsion base of claim 1, wherein the base is stable for at least three cycles of freeze and thawing.

7. A composition comprising the thin emulsion base of claim 1 and a floral fragrance.

8. A composition comprising the thin emulsion base of claim 1 and at least one compound selected from the group consisting of caprylic/capric triglyceride, cyclomethicone or dimethicone, glycols, glycerin, and sodium hyaluronate.

9. A composition comprising the thin emulsion base of claim 1 and at least one compound selected from the group consisting of peptides, xanthan gum, PEGs, ceramides, and retinoids.

10. A composition comprising the thin emulsion base of claim 1 and at least one compound selected from the group consisting of coco-glucoside, glycerin, PEGs, and decyl glucoside.

11. A composition comprising the thin emulsion base of claim 1 and sunflower seed oil.

12. A composition comprising the thin emulsion base of claim 1 and tocopherol.

13. A method of manufacturing a thin emulsion base for cosmetic products by combining a solvent, an alkane texture enhancer, and a lipid emulsifier, wherein:
   i) the solvent is a plant juice derived supernatant having 6-20% w/w carbohydrate content, an acidic pH of between 2.2 to 6.0, and a bacterial cell count of less than 150 CFU/g, wherein the amount of the solvent ranges from 85 to 86% w/w of the total weight of the thin emulsion base;
   ii) the alkane texture enhancer is a mixture consisting of at least 90% w/w C12 alkanes, less than 10% w/w C14 alkanes, and less than 10% w/w coco-caprylate/caprate;

iii) the lipid emulsifier is a mixture consisting of 30 to 60% w/w polyglyceryl-10 mono/dioleate, 30 to 60% w/w polyglyceryl-3 oleate, 3 to 7% w/w glycerin, and 0.5 to 1.5% w/w phosphatidylglycerol;

wherein the weight to weight ratio of the alkane texture enhancer to the lipid emulsifier of the thin emulsion base is 1; and wherein the thin emulsion base is stable for at least 90 days at 40° C.

* * * * *